(12) United States Patent
Dessipri et al.

(10) Patent No.: US 6,639,044 B2
(45) Date of Patent: Oct. 28, 2003

(54) USE OF NIR (NEAR-INFRARED SPECTROSCOPY) IN COMPOSITE PRODUCTION

(75) Inventors: Eugenia Dessipri, Thessaloniki (GR); Georgios D. Chryssikos, Athens (GR); Vassilis Gionis, Athens (GR); Alkiviadis Paipetis, Athens (GR); George Kalousis, Thessaloniki (GR)

(73) Assignee: Enigma N.V., Curacao (AN)

( * ) Notice: Subject to any disclaimer, the term of this patent is extended or adjusted under 35 U.S.C. 154(b) by 0 days.

(21) Appl. No.: 09/886,947

(22) Filed: Jun. 21, 2001

(65) Prior Publication Data
US 2002/0128398 A1 Sep. 12, 2002

(51) Int. Cl.[7] .................................................. C08G 8/10
(52) U.S. Cl. ........................ 528/230; 528/129; 528/256; 430/627; 430/495.1; 250/339.09
(58) Field of Search ............................... 528/230, 129, 528/256; 430/627, 495.1; 250/339.09

(56) References Cited

U.S. PATENT DOCUMENTS 5,965,888 A * 10/1999 Engstrom et al. ...... 250/339.09

OTHER PUBLICATIONS

Mouratidis, P.I., et al. "New Adhesive System for Improved Exterior–Grade Wood Panels", *Wood Adhesives 2000*, pp. 197–204.
Dunkers, J.P., et al. "Fourier Transform Near–Infrared Monitoring of Reacting Resins Using an Evanescent Wave High–Index Fiber–Optic Sensor", *Applied Spectroscopy*, (1998), 52(4), pp. 552–556.
Fischer, D., et al. "In–line process monitoring on polymer melts by NIR–spectroscopy", *Fresenius J. Anal. Chem.*, (1997), 359: pp. 74–77.
DeThomas, F.A., et al. "Real–Time Monitoring of Polyurethane Production Using Near–Infrared Spectroscopy", *Talanta*, (1994), 41(3): pp. 425–431.
Hall, J.W. and F.A. DeThomas. "Monitoring the Production of Polyurethanes with Near–Infrared Spectroscopy", *35th Annual Polyurethane Technical/Marketing Conference*, Oct. 9–12, 1994, pp. 381–383.
DeThomas, F.A. and J.W. Hall. "Controlling the Process". NIR Systems, Inc., Silver Spring, MD.
"Squeezing More Capacity from Your Plant with NIRSystems Process Analytics". NIRSystems Process Analytics Advertisement.
T.K. McMahon. "Process Control and Manufacturing Efficiency", *Control*, (Nov. 1996).
Ghosh, S. and G. L. Brodmann. "On–Line Measurement of Durable Press Resin on Fabrics Using the NIR Spectroscopy Method", *Textile Chemist and Colorist*, (Apr. 1993), 25(4): pp. 11–14.
Reshadat, R., et al. "Quality Monitoring of Recycled Plastic Waste During Extrusion: I.In–Line Near–Infrared Spectroscopy", *Antec*, (1994), pp. 2227–2231.
C. Kniest. "Charakterisierund vond Span–Leim–Geimschen mittels NIR Spektroskopie", *Holz als Roh–und Werkstoff*, (1992), 50: pp. 73–78.

* cited by examiner

Primary Examiner—Duc Truong
(74) Attorney, Agent, or Firm—Ladas & Parry

(57) ABSTRACT

A method for controlling the production of formaldehyde resin compositions in which formaldehyde takes part in a reaction with one or a combination of co resin forming material (of the type phenol, urea, melamine) the method includes monitoring at least one of the formation of the reaction mixture and the course of the reaction by near-infrared (NIR) spectroscopy and adjusting the course of the reaction (when necessary) in accordance with the results of the spectroscopy to obtain optimum conditions for the reaction.

18 Claims, 4 Drawing Sheets

USE OF NIR (NEAR-INFRARED SPECTROSCOPY) IN COMPOSITE PRODUCTION

Figure 1:
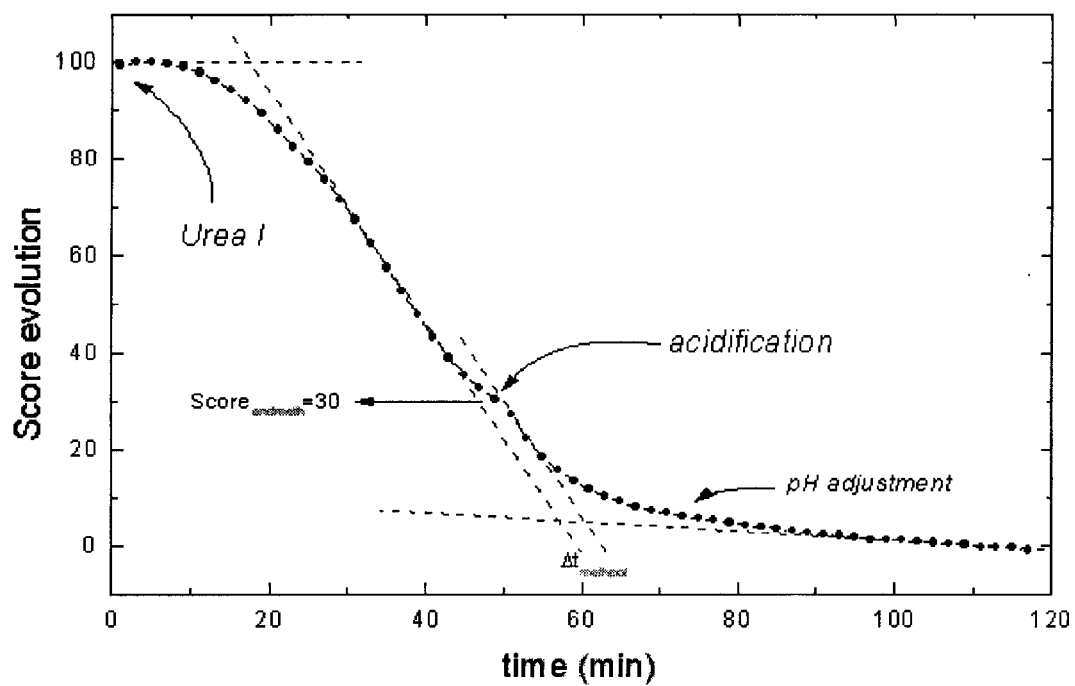

The present invention relates to the use of a spectroscopic method (NIR (Near-infrared spectroscopy)) for monitoring an industrial process (production of resin bonded composites particularly formaldehyde resin bonded composites) from the analysis of raw materials and intermediate products (such as urea-formaldehyde concentrates) to the quality control of the final product.

The use of NIR spectroscopy to monitor various processes has been developed systematically during the last years and was assisted by the increase in speed and capacity of the computers available. This NIR technique has been applied to various industries such as the oil industry, pharmaceuticals, food industry, control of fermentation, and certain polymer manufacture. There has been the use of the system in on line and end point determinations and reaction coordination for homogeneous and heterogeneous reactions. The analysis has been carried out on liquid and vapor phase process streams. In line process monitoring on polymer systems by NIR spectroscopy is discussed by D. Fischer et al., Fresenius J. Anal. Chemistry, 359 (1997) page 74 and J. Dunkers et al, Fourier Transform-NIR monitoring of Reacting Resins Using an Evanescent Wave High Index Fiber optic Sensor, Applied Spectroscopy, 52 (4), 1998, page 552. In particular the use of the system has been described in particleboard (composite board) manufacturing for monitoring raw wood quality (B. Engstrom and Mona Hedqvist, Prediction of the Properties of board by using a spectroscopic method combined with multivariate calibration, U.S. Pat. No. 5,965,888).

The manufacturing of composite wood-based panels (particleboard, medium density fiberboard, etc.) originated from a market need to provide inexpensive wood product alternatives and relied originally on the use of urea-formaldehyde adhesives. At high formaldehyde to urea ratios (F/U≈1.5 molar), these water-based adhesives are easy to make and use, and give excellent bonding results to almost any kind of wood chip. Around 1978, environmental concerns for formaldehyde emission imposed lower F/U ratios (≈1) that brought up the need for a much more careful and systematic control of the adhesive production. Furthermore, it was proposed that urea-formaldehyde concentrate (UFC) be used instead of formalin as a raw material for the preparation of the adhesives, in order to reduce the costs and hazards of transportation and to avoid the application of vacuum for the distillation of the excess water at the end of resin production. Despite its merits, only very few manufacturers implement today the UFC approach, because of its chemical complexity and the lack of quick methods for its characterization. Formaldehyde-based adhesives are made reliably by relatively large companies that have developed semi empirical know-how and can afford occasional application of costly and time consuming off-line monitoring techniques (GPC, NMR, etc.).

UFC is an intermediate for the resin synthesis that is typically prepared, by a continuous process, in an absorption tower. During this process gaseous formaldehyde is absorbed by an aqueous solution of urea. Absorption involves both dissolution of formaldehyde as well as chemical reaction of formaldehyde with urea. The ratio of urea to formaldehyde and the total solids content, pH, and temperature vary along the absorption tower and are important for the quality of the final product and the safe continuous production. Irregularities in the process can result in insoluble precipitate formation along the length of the tower or even blocking of intermediate disks of the tower.

The final product is a complex mixture of at least fifteen different compounds. The precise determination of the urea and formaldehyde content in these compounds is essential for the subsequent formulation of the resin. Conventionally it is performed only off line by tedious methods. One such method involves the hydrolysis of the UFC to obtain formalin that is subsequently extracted and after numerous dilutions; its concentration is finally determined by titration. The concentration of urea is calculated independently by determining the total nitrogen concentration (Kjeldahl method). The overall determination of formaldehyde and urea content with these methods takes more than four hours. Faster chromatographic methods have been developed but they are less accurate and require precise sample weighting and specific equipment. Furthermore, they cannot be applied on line. The above methods can only determine the overall content of urea and formaldehyde and give no information on the existing chemical speciation.

The UFC produced is subsequently used for the resin production (conventionally performed in a batch process). (Alternatively, formalin, that does not contain any urea, can be used for the resin production). The process of resin production is influenced by the raw materials used and the conditions applied and particularly the pH and concentration of the various components at every particular time. Failing to terminate the reaction at the correct conversion level can result in crosslinking of the resin and formation of an insoluble network inside the reactor. Furthermore, variability of resin production can result in variations in resin's performance that are decreasing the reliability to the customers.

An objective of the invention is to provide a methodology for the control of all the raw materials and intermediate products (methanol, formaldehyde, urea, urea solutions, UFC, melamine, etc.) involved in formaldehyde based resin synthesis.

Particularly for the case of UFC the objective of the present invention is to provide a methodology for the fast and reliable determination of its content in urea and formaldehyde. Furthermore this methodology will be adaptable to on-line monitoring of the UFC production process. Therefore the urea and formaldehyde content will be measured continuously and at various points along the absorption tower in order to ensure regular production or detect irregularities.

Another objective of the invention is to provide a methodology for monitoring the resin production and for ensuring the reproducibility of the final product.

It has surprisingly been found that NIR can be used for the determination of the overall content of urea and formaldehyde in UFC even though the latter is a complex mixture of more than 15 different compounds containing urea and formaldehyde.

It has also been surprisingly found that NIR can be used for the monitoring of reactions of urea and formaldehyde in the production of a UF resin. This enables the monitoring of the start of methylolation through to the ending of polymerization so as to an evaluation of the various stages of the production. Again it was surprising to find that NIR could be used for the monitoring of such a polymerization despite the complex mixture of different compounds formed during the polymerization.

According to a first aspect of the invention there is provided a method for controlling the production of formaldehyde resin compositions in which formaldehyde takes part in a reaction with one or a combination of co resin forming material (of the type phenol, urea, melamine) the method comprising monitoring at least one of the formation of reaction mixture and the course of the reaction by near-infrared (NIR) spectroscopy and adjusting the course of the reaction (when necessary) in accordance with the results of the spectroscopy to obtain optimum conditions for the reaction.

According to the second aspect of the invention there is provided a method for controlling the production of formaldehyde resin compositions in which formaldehyde takes part in a reaction with one or a combination of co resin forming material, the method comprising monitoring at least one of the formation of the reaction mixture and the course of the reaction by near-infrared (NIR) spectroscopy, adjusting the course of the reaction (when necessary) in accordance with the results of the spectroscopy to obtain optimum conditions for the reaction wherein said monitoring is effected by comparing near infra red spectra obtained periodically from the reaction mixture or data computed therefrom with measurements or data calculated previously during calibration of the system.

According to a third aspect of the invention there is provided a method for assessing the performance of formaldehyde-based resins, the method comprising subjecting the resin to near-infrared spectroscopy to determine the spectra of the resin and comparing the spectra so determined to reference spectra of resins of known performance.

The accuracy of the above determination is surprising in view of the fact that the region of the spectra used in the analysis contains combination bands that are influenced by the strong hydrogen bonding interactions known to be present.

It was also surprising that a batch polymerization process could be monitored from the beginning to the end with a single optical path, even though the cloudiness changes drastically during the process.

The methodology developed involves the use of a Fourier-Transform NIR (FT-NIR) spectrometer, in a fiber optic acquisition mode. A typical procedure involves the selection of the optical resolution and acquisition time in order to allow for the optimum accuracy and signal to noise ratio with the minimum acquisition time. For the acquisition of the spectra the probe has to be immersed in the sample that is measured. Customized software can allow for automated acquisition of spectrum, data treatment, and results analysis and display. When on-line measurements are performed spectra acquisition can be programmed to take place at specified intervals of time.

Thus one embodiment of the invention is a method in which the reaction is between formaldehyde and urea and the monitoring is carried out during the formation of resin by reaction of formaldehyde and urea with a view to optimizing the formation of the final resin.

A particular embodiment of the invention is a method in which the spectroscopy measure is applied to the preparation of urea formaldehyde concentrate (UFC) to provide a high quality intermediate for urea formaldehyde resin synthesis.

The control of the invention can be applied to various formaldehyde reactions of the resin forming components. Thus the reaction can be applied not merely to reactions of formaldehyde and urea but the reactions of formaldehyde and phenol or melamine. The nature of the secondary component would be immediately apparent to those skilled in the art since the manufacture of formaldehyde resins is well known and the nature of the other reacting component is also well known.

The particular embodiment involving application and preparation of UFC can be effected in an absorption tower wherein gaseous formaldehyde is absorbed by an aqueous solution of urea.

For example for the determination of the urea and formaldehyde content of UFC calibration is necessary. For this purpose, a chemometric algorithm can be used, based on the original spectra or on their derivatives. The method must be built on a database of a significant number of UFC samples for which formaldehyde and urea contents must be measured independently. More than one spectrum from each sample can be obtained at a specified temperature. The selection of the temperature depends on the specific application of the method that is developed. However, it was found that it is important to perform all measurements at the same temperature. Validation of the method involves removing each spectrum from the database and treating it as an unknown in order to quantify the accuracy of the prediction. The sample's content in urea and formaldehyde can be determined using the remaining spectra. The resulting root mean square error of the estimation for the database has to be lower than 0.5 for both the urea concentration and the formaldehyde concentration. Typical application (see example 1) gives much better RMSEP (Rout Mean Square Error of Prediction) than this. Furthermore a conformity test will be provided in order to ensure that the UFC does not deviate from its statistical composition (not just the overall urea and formaldehyde content but also the specific ingredients). A similar method can be developed for on line control. In this case spectra acquisition can be performed automatically at specified intervals of time, for instance every 15 minutes or less.

As mentioned the process can also be used for monitoring resin synthesis for example reaction of formaldehyde and urea.

In another specified embodiment the near infrared spectroscopy monitoring is effected on a urea/formaldehyde reactor to define a pathway for formation of a urea/formaldehyde resin with adjustment of any deviations found by the spectroscopy when these are greater than the defined optimum pathway.

For further monitoring the process of resin synthesis, a probe should be installed in the reactor and acquisition of data should be performed at short time intervals (for instance every 2 minutes). Algorithms can be created for monitoring applications. One such algorithm, describes the system in a multidimensional vectorial space, assigns arbitrary values to at least two extreme situations encountered during the synthesis process in order to create a scale and interpolates any intermediate spectrum within these two or more standards. Other algorithms describe quantitatively band intensities or the position of frequency extremes specifically corresponding to reactants, intermediates, final products, or unwanted by-products. The time evolution of these scores allows the phenomenological monitoring of each reaction. Statistical evaluation of the time evolution of these scores for each type of resin synthesis allows for defining the "pathway" that should be followed in a particular resin synthesis and of the maximum deviations from this pathway that still lead to the acceptable final product. Deviations larger than those defined as maximum are not acceptable and therefore result in a warning signal for the operator.

Thus the process of the invention can be used to monitor the production of starting materials such as urea formaldehyde concentrates for the use of raw materials, urea and formaldehyde for such UFC in the production of the final resin. Similarly the process is equally easily applicable to production of intermediates and final resin production for such resins as melamine formaldehyde and phenol formaldehyde resins. As stated earlier, it was surprising to find that FT-NIR spectroscopy could be used in such complex systems despite the use of FT-NIR spectroscopy for monitoring other types of reactions.

The course of the reaction can be adjusted as follows dependent on the prevailing conditions:
a) An undesirable fast initial rate of methylolation in the synthesis of UF can be observed with NIR and corrected by adjusting the pH;
b) An undesirable fast polymerisation can be observed by NIR and corrected either by increasing the pH or decreasing the temperature;
c) An undesirable slow polymerisation can be corrected by decreasing the pH or increasing the temperature; and
d) Incomplete methylolation can be detected by NIR and adjusted by prolonging the methylolation stage or increasing the temperature.

The above examples are given by way of example and are not nor are they intended to be exhaustive.

The adjustment process can be automated if required. Here the NIR readings are used to control various physical parameters such as acid and/or alkali additions to the resin constituents to control pH and burners or electrical heaters to control the temperature of the resin composition.

EXAMPLE 1
Determination of Urea and Formaldehyde Content of UFC

A method is created that runs in the OPUS OS/2 environment and consists of two OPUS IBM OS2 compatible files with extensions *.Q2 and *.222. It is based on 40 NIR spectra of UFC obtained with a 1 mm path quartz fibre at 25±1° C. Each spectrum is assigned three values for urea content, formaldehyde content and refractive index respectively which are independently measured.

In order to execute the method, the files associated with it (with extensions *.Q2 and *.222) should be copied to a separate directory. Input spectra of unknown UFC should be acquired by the standard experiment, i.e. 1 min acquisition time at resolution 8 $cm^{-1}$. Under these conditions, 101 scans are performed. Measurements should be made at a steady temperature of 25±1° C.

Spectra of UFC samples can be analyzed independently or in groups (Make or Load File List). In both cases, reports are produced automatically. These reports can be either viewed through OPUS or printed to .txt files, and then opened with any Windows editor or spreadsheet (such as Microsoft Word or Excel).

The method can be modified either with the exclusion/addition of existing spectra or with the addition of reference spectra together with the respective variable values. Each time the method is changing, it should be re-calibrated to include the modifications (a new calibration file is then created with incrementing extension i.e. *.223, *.224 etc.).

The respective RMS error for the calibration datasets are:

|  | RMS ERROR | | |
| --- | --- | --- | --- |
| METHOD: UFCNHRFb.Q2 | UREA | FORMOL | RI |
| Calibrated dataset: S078 | 0.14 | 0.08 | 0.0001 |

The method is limited by the accuracy of the input values.

EXAMPLE 2
Monitoring UF Resin (Molar Ratio 1,15) Synthesis at Laboratory Scale.

The probe was immersed in the reaction vessel and spectra acquisition was performed with an automated acquisition program every 2 min. Each spectrum is an average of 100 scans (1 min acquisition time). The procedure was repeated for several times in order to assess the level of reproducibility. Subsequently, an algorithm was built. The algorithm assigned the arbitrary value of 100 to the starting of methylolation and 0 to the ending of polymerization and interpolated linearly any intermediate spectrum within these two standards. The time evolution of these scores allowed the phenomenological monitoring of each synthesis. FIG. 1 depicts the trace resulting from the application of the algorithm to a reaction.

Figure 2:
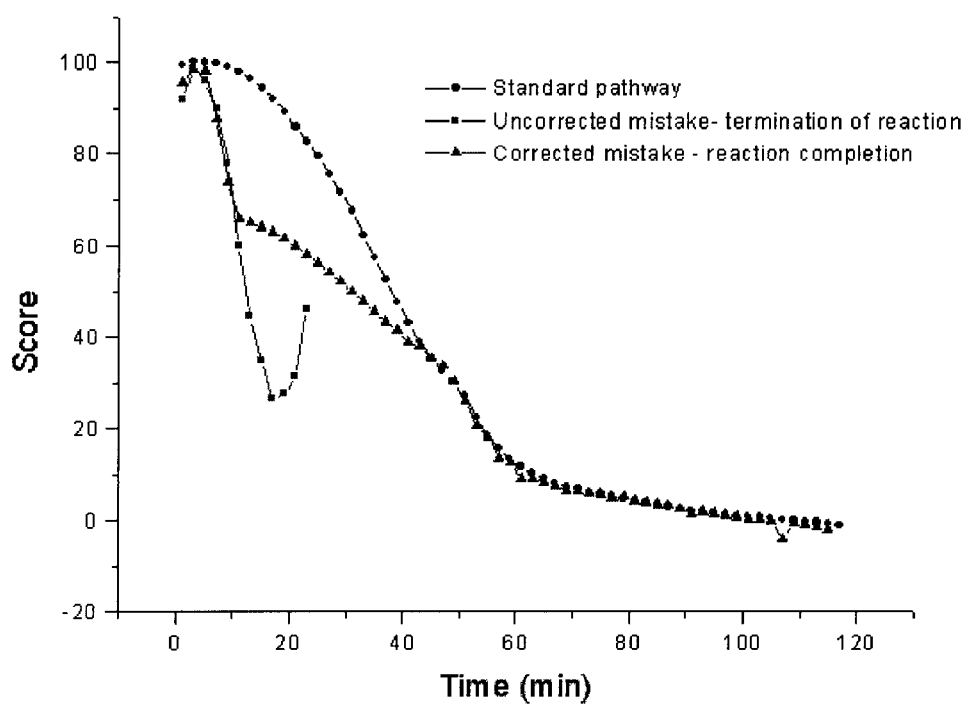

In order to demonstrate the usefulness of the methodology in detecting and correcting mistakes a deliberate mistake was made in the beginning of the reaction (FIG. 2). Monitoring with NIR enabled the detection of the mistake as deviation from the standard pathway. The mistake was detrimental and further resins synthesis was stopped. Subsequently, the same mistake was repeated, but it was corrected after detection. As seen in FIG. 2 the reaction followed initially a different pathway but after correction gave the same final product.

EXAMPLE 3
Monitoring the Polymerization of UF Resin (Molar Ratio 1,15) at Laboratory Scale.

Figure 3:
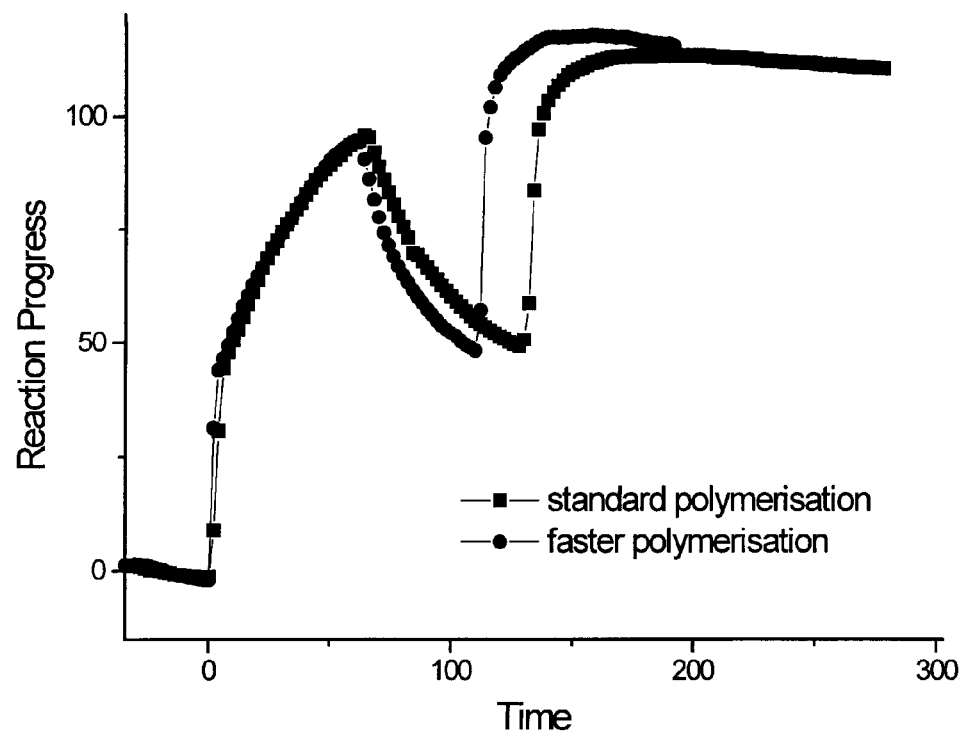

Acquisition of data was performed as in Example 2. A new algorithm was built that is particularly sensitive to the polycondensation reaction. The time evolution of the scores obtained with this algorithm allowed the monitoring of various synthesis. Repetition several times allowed the definition of the standard pathway. FIG. 3 depicts the trace resulting from the application of the method. The method clearly provides a means to detect a faster than the standard polymerization reaction and therefore prevent from over passing the allowable conversion level.

EXAMPLE 4
Monitoring the Production of UF Resin at Industrial Scale.

Figure 4:
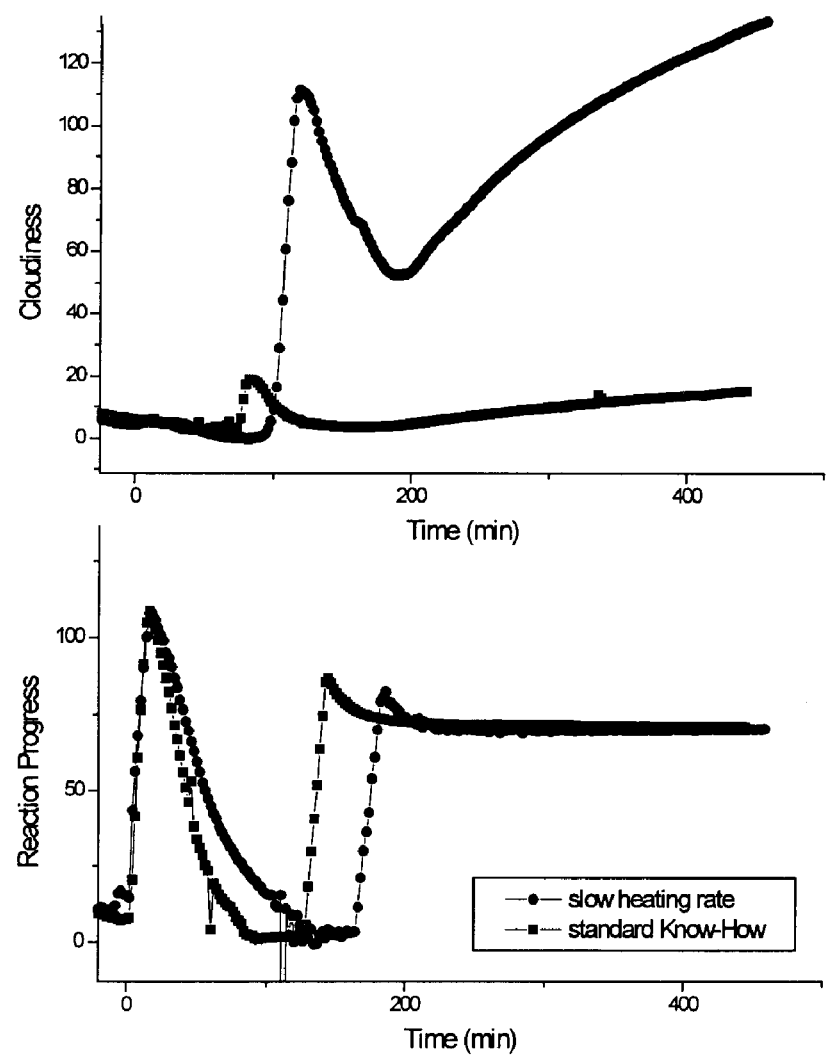

Suitable process probe was used and adapted to a 25-ton reactor. Data were collected and translated automatically to reaction pathways using custom-made software. Monitoring of several production batches showed that the major source of irreproducibility was the variation of the heating rate during the step of methylolation (FIG. 4). The optimum heating rate was found and correlated with the cloudiness of the reaction mixture during the polymerization as well as the cloudiness and stability of the final product. The example shows that the method can be used for the optimization of the production process.

NIR spectroscopy can be equally well employed to evaluate the final resin even if its synthesis has not been monitored by NIR. The calibration and validation algorithm necessary for this is built on a database that consists of spectra of resins of known composition and performance. The algorithm can be used to correlate the spectra with the performances or to check the conformity of a resin with unknown performance to a set or reference resins of good performance. The algorithm can be based on parts of the original spectra or their derivatives. The parts of the spectra selected can be chosen on the basis of the chemical assignments, or empirically. Since the performance of resins depends on the particular conditions under which they are used it is apparent that variations of the method should be available for various applications of the same type of resins.

With suitable calibration, the process can also be used to evaluate the performance of formaldehyde based resins, the production of which has not been monitored by NIR.

The NIR monitoring described in Examples 1 to 4 can of course be accompanied with the reaction adjustment (as necessary).

What is claimed is:

1. A method for controlling the production of formaldehyde resin compositions in which formaldehyde takes part in a reaction with at least one co-resin forming material in an aqueous reaction solution, the method comprising monitoring at least one of the formation of the reaction solution and the course of the reaction in the solution by near-infrared (NIR) spectroscopy and, if necessary, adjusting the course of the reaction in accordance with the results of the spectroscopy to obtain optimum conditions for the reaction.

2. A method according to claim 1 wherein said co-resin forming material is selected from the group consisting of phenol, urea, melamine and mixtures thereof.

3. A method according to claim 1 in which the reaction is between formaldehyde and urea and the monitoring is carried out during the formation of resin by reaction of the formaldehyde and urea with a view to optimizing the process of formation of the final resin and to prevent mistakes that result in production loss.

4. A method according to claim 1 in which the near-infrared spectroscopy monitoring is applied to the preparation of urea formaldehyde concentrate (UFC) to provide a constant high quality intermediate for urea formaldehyde resin synthesis.

5. A method according to claim 4 in which the monitoring is effected in an absorption tower wherein gaseous formaldehyde is absorbed by an aqueous solution of urea.

6. A method according to claim 1, wherein the near-infrared spectroscopy monitoring is effected on a urea formaldehyde reactor to define a pathway for formation of a formaldehyde based resin with adjustment of any deviations found by the spectroscopy when these are greater than the defined optimum pathway.

7. A method according to claim 2 wherein the near-infrared spectroscopy monitoring is effected on a reactor to define a pathway for formation of a formaldehyde based resin with adjustment of any deviations found by the spectroscopy when these are greater than the defined optimum pathway.

8. A method for controlling the production of formaldehyde resin compositions in which formaldehyde takes part in a reaction with at least one co-resin forming material in an aqueous reaction solution, the method comprising monitoring at least one of the formation of the reaction solution and the course of the reaction in the solution by near-infrared (NIR) spectroscopy, and, if necessary, adjusting the course of the reaction in accordance with the results of the spectroscopy to obtain optimum conditions for the reaction, wherein said monitoring is effected by comparing near-infrared spectra obtained periodically from the reaction solution or data computed therefrom with measurements or data calculated previously during calibration of the system.

9. A method as claimed in claim 8, wherein said comparison is made with a calculated number which has been derived from measurements of near-infrared spectra for formaldehyde and co-reactant solutions at least two different points during the reaction or formation of the reaction solution.

10. A method as claimed in claim 8 wherein said co reactant is selected from the group consisting of phenol, melamine, urea and mixtures thereof.

11. A method for assessing the performance of a formaldehyde-based resin, the method comprising subjecting an aqueous solution comprising the resin to near-infrared spectroscopy to determine the spectra of the resin and comparing the spectra so determined to a reference spectra of resins of known performance.

12. A method as claimed in claim 11 in which the spectroscopy is of the vibrational type and the comparison of the chemometric type.

13. The method according to claim 1, wherein the monitoring comprises immersing a probe into the reaction solution to obtain spectra from the reaction solution.

14. The method according to claim 13, wherein the course of the reaction is adjusted in accordance with the spectra.

15. The method according to claim 14, wherein the course of the reaction is adjusted by adjusting the pH or temperature of the reaction solution.

16. The method according to claim 8, wherein the monitoring comprises immersing a probe into the reaction solution to obtain spectra from the reaction solution.

17. The method according to claim 16, wherein the course of the reaction is adjusted in accordance with the spectra.

18. The method according to claim 17, wherein the course of the reaction is adjusted by adjusting the pH or temperature of the reaction solution.

\* \* \* \* \*

UNITED STATES PATENT AND TRADEMARK OFFICE
CERTIFICATE OF CORRECTION

PATENT NO. : 6,639,044 B2
DATED : October 28, 2003
INVENTOR(S) : Eugenia Dessipri et al.

It is certified that error appears in the above-identified patent and that said Letters Patent is hereby corrected as shown below:

<u>Title page,</u>
Insert item
-- [30] Foreign Application Priority Data   Dec. 22, 2000   (GB) .... 0031522.6 --.

Signed and Sealed this

Tenth Day of February, 2004

JON W. DUDAS
*Acting Director of the United States Patent and Trademark Office*